United States Patent [19]

Tim-Wo Chu et al.

[11] B  4,001,265
[45] Jan. 4, 1977

[54] 3,4-DIMETHYL-5-ISOXAZOLYLSUL-FAMYLANILINE

[75] Inventors: Daniel Tim-Wo Chu, Greenfield Park; David Lyon Garmaise, Montreal, both of Canada

[73] Assignee: Abbott Laboratories, North Chicago, Ill.

[22] Filed: Mar. 3, 1975

[21] Appl. No.: 554,848

[44] Published under the second Trial Voluntary Protest Program on February 24, 1976 as document No. B 554,848.

Related U.S. Application Data

[62] Division of Ser. No. 378,305, July 11, 1973, Pat. No. 3,894,061.

[52] U.S. Cl. .............................. 260/307 H; 424/19; 424/228

[51] Int. Cl.$^2$ ..................................... C07D 261/16
[58] Field of Search ..................... 260/239.9, 307 H

[56] References Cited
UNITED STATES PATENTS

| | | | |
|---|---|---|---|
| 3,671,539 | 6/1972 | Saucy | 260/307 H |
| 3,689,498 | 9/1972 | Lumgruber et al. | 260/307 H |

Primary Examiner—Dale R. Ore
Attorney, Agent, or Firm—Paul D. Burgauer; Robert L. Niblack

[57] ABSTRACT

A specific anilino derivative of chelocardin having high antibiotic activity is described. This new derivative shows unusually low toxicity and consequently a very high therapeutic index as chemotherapeutic agent against gram-negative organisms.

2 Claims, No Drawings

3,4-DIMETHYL-5-ISOXAZOLYLSULFAMYLANILINE

This is a division of application Ser. No. 378,305 filed July 11, 1973 now U.S. Pat. No. 3,894,061.

DETAILED DESCRIPTION OF THE INVENTION

Chelocardin is the name assigned to the antibiotic M-319 originally described in U.S. Pat. No. 3,155,582 issued in 1964. The original publication did not disclose the chemical structure, but since then, the structure has been elucidated (see J.A.C.S., 92, page 6070 of 1970) and as a result of this knowledge, new derivatives were prepared. Unfortunately, predicting physiological activity of such new derivatives is impossible, but surprisingly, a new group of compounds have now been found that share and even exceed the chemotherapeutic activity of chelocardin itself while showing some advantageous physical and/or chemical properties.

The new compounds which are the subject of the present invention is the substituted anilino derivative of chelocardin, having the following structure:

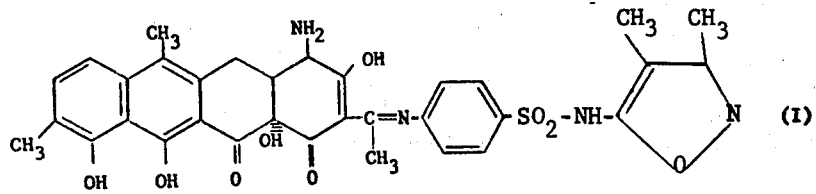

or nontoxic acid addition salts thereof, or the corresponding tautomeric forms thereof.

The new compound can easily be prepared by reacting cheleocardin with a slight molar excess of 3,4-dimethyl-5-isoxazolylsulfamylaniline. in an inert, organic solvent or an aqueous mixture therewith. The term "inert" is used herein to express that the solvent does not react or interfere with any of the starting materials or the formed end product. A preferred reaction medium is aqueous tetrahydrofuran (hereinafter simply referred to as THF) wherein the THF contains between 0.1 to 5 percent by volume of water. However, good results are also obtained when the reaction medium is methanol, ethanol or the like.

In a preferred embodiment, a nontoxic acid addition salt of chelocardin or chelocardin itself is combined with the 3,4-dimethyl-5-isoxazolylsulfamylaniline in an inert, organic solvent and the solution is allowed to stand for between 1 hour and several days at room temperature. Reaction times beyond 24 hours usually add no further benefit and in most instances, the condensation is essentially complete in 1–8 hours. If desired, the temperature of the reaction medium may be raised but since room temperature is usually adequate, no need exists to heat the mixture beyond 70° C. A preferred reaction solvent is THF containing 5 percent of water. If chelocardin base is the starting material, the condensation product of formula I is obtained. If the starting material is an acid addition salt, the final product is the corresponding acid addition salt of the compound of formula I. In either case, the base can easily be converted to the desired salt and the salt can easily be converted to the base in routine and known fashion.

In order to illustrate the manner of preparing the new compounds, reference is made to the following examples which, however, are not intended to limit the invention in any respect. The thin-layer and spectrographic data obtained were in agreement with the assigned structure. The new p-substituted aniline moiety was found in the 2α-position of chelocardin.

EXAMPLE 1

A solution of 150 mg. of acetic acid in 1 ml. of THF is added to 365 mg. chelocardin hydrochloride dissolved in 25 ml. of THF. After adding 365 mg. of 3,4-dimethyl-5-isoxazolylsulfamylaniline, the solution is heated to 50° C. in a nitrogen atmosphere for three days. Ether (20 ml.) is then added and the suspension is filtered; the residue is washed twice with 20 ml. portions of ether, yielding 500 mg. (90%) of the 3,4-dimethylisoxalylsulfamylanilino-chelocardin hydrochloride.

EXAMPLE 2

In order to show the antibiotic and bacteriostatic activity of the compound of the present invention, the minimum inhibitory concentrations (MIC) are demonstrated in Table I below. The bacteria are first grown in a brain-heart infusion broth for 24 hours at the optimum temperature for the organism. The culture is then diluted with water so that there are about 10 Mio. viable organisms per milliliter. The cell suspension is used as the inoculum for the tests reported below. The test compound, about 20 mg. is dissolved in 0.2 ml. of methanol and 19.8 ml. of water. The various test solutions of varying concentrations are well distributed in agar suspensions adjusted to a pH of 7.4 and placed in Petri dishes so that each dish contains a known amount of test compound.

The surfaces of the solidified agar plates are then inoculated with the test culture by streaking the test culture on the surface of the plate with a standardized loop that has been dipped in the inoculum and incubated at room temperature for 24 hours. The MIC values in Table 1 are expressed in mcg./ml.

TABLE 1

| Compd. of Ex. | Staph. Aureus 45 | Staph. Aureus Smith | S. Pyogenes C-203 | Enterococcus 89 | Escher. Coli Juhl | Kleb. Pneum. 8045 | Past. Mult. 10544 | Pseudo. Aerugi BMH No. 10 | Prot. Vulg. ABB JJ | Prot. Mira. Fin. 9 | Salm. Typhi. Ed. 9 | D. pneumon. 6301 |
|---|---|---|---|---|---|---|---|---|---|---|---|---|
| 1 | 6.2 | 6.2 | 6.2 | 12.5 | 6.2 | 3.1 | 0.78 | 50 | 3.1 | 12.5 | 1.56 | 6.2 |

As shown in Table 1, the compound of the present invention exhibits valuable bacteriostatic properties and is consequently useful in pharmaceutical compositions. The salts of this invention also exhibit very low oral and subcutaneous toxicities and produce generally the same antibiotic activities in vivo as chelocardin.

In addition to the excellent bacteriostatic properties of the new compounds, they also show a surprising physical characteristic: they are more soluble in water than chelocardin and therefore, the new compounds distinguish favorably over chelocardin itself. The excellent solubility makes the new compounds particularly suitable for parenteral solutions which can easily be prepared by simply dissolving the new chelocardin derivatives in water which may be buffered to a pH of 7.0 to 7.8 and may contain 0.5–5 percent by weight of a preservative such as benzyl alcohol.

Preferably, the new derivative is used in the form of its acid addition salts with pharmaceutically acceptable acids, i.e., hydrochloric, sulfuric, acetic, phosphoric, tartaric, citric or succinic acid. Since hydrochloric acid forms a stable acid addition salt with the new compound and such salt is suitable for pharmaceutical preparations and can be easily prepared, it is preferred.

For oral dosage forms, tablets, pills, wafers, suspensions, syrups, etc. can be prepared in standard fashion using the usual pharmaceutically acceptable excipients such as carriers, diluents, pigments, dyes and coatings. The coatings for tablets may be of the kind that dissolves rapidly in the acidic environment of the stomach, or a sustained-release coating formulation may be selected to provide a gradual release of the active ingredient over an extended period of time in order to maintain a bacteriostatic blood level over periods ranging from 2–24 hours.

For the treatment of smaller animals, a daily dose of 10–200 mg./kg. is recommended for oral administration. For larger animals, including humans, a daily oral dose of 50–800 mg./day produces a desirable antibiotic activity. Oral dosages are preferably prepared in unit dosage form with the dosage selected in such amounts that a single or several doses are administered over a 24 hour period.

What is claimed is:
1. A compound of the formula:

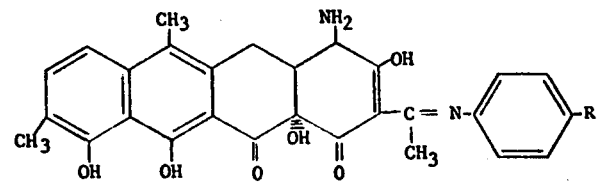

wherein R is 4-dimethyl-5-isoxazolylsulfamyl or the corresponding tautomeric form or a pharmaceutically acceptable acid addition salt thereof.

2. The compound of claim 1 wherein R is 3,4-dimethyl-5-isoxazolylsulfamyl.

* * * * *

UNITED STATES PATENT AND TRADEMARK OFFICE
CERTIFICATE OF CORRECTION

PATENT NO. : 4,001,265
DATED : January 4, 1977
INVENTOR(S) : Daniel Tim-Wo Chu and David Lyon Garmaise It is certified that error appears in the above-identified patent and that said Letters Patent are hereby corrected as shown below:

In column 4, line 26, Claim 1, delete "4-dimethyl-5-isoxazolylsulfamyl and substitute therefor -- 3,4-dimethyl-5-isoxazolylsulfamyl --.

*Signed and Sealed this*

Twenty-sixth Day of April 1977

[SEAL]

Attest:

RUTH C. MASON
*Attesting Officer*

C. MARSHALL DANN
*Commissioner of Patents and Trademarks*